United States Patent [19]
Katsuragi et al.

[11] Patent Number: 5,337,095
[45] Date of Patent: Aug. 9, 1994

[54] OPHTHALMOLOGICAL INSTRUMENT

[75] Inventors: Kenjiro Katsuragi; Akira Tanabe, both of Tokyo, Japan

[73] Assignee: Kabushiki Kaisha Topcon, Tokyo, Japan

[21] Appl. No.: 963,048

[22] Filed: Oct. 19, 1992

Related U.S. Application Data

[63] Continuation of Ser. No. 513,275, Apr. 24, 1990, abandoned.

[30] Foreign Application Priority Data

Apr. 26, 1989 [JP] Japan ................. 1-106351

[51] Int. Cl.5 ............................................. A61B 3/14
[52] U.S. Cl. ................................ 351/208; 351/205
[58] Field of Search ............... 351/205, 206, 208, 211, 351/212, 214, 221

[56] References Cited

U.S. PATENT DOCUMENTS

| 4,712,894 | 12/1987 | Nunokawa | 351/208 |
| 4,786,161 | 11/1988 | Müller et al. | 351/205 |
| 4,991,953 | 2/1991 | Pflibsen et al. | 351/206 |

*Primary Examiner*—William L. Sikes
*Assistant Examiner*—Hung Xuan Dang
*Attorney, Agent, or Firm*—Finnegan, Henderson, Farabow, Garrett & Dunner

[57] ABSTRACT

An ophthalmological instrument has an anterior portion observation system for observing the anterior portion of an eye to be tested. The anterior portion observation system includes focus position shifting means capable of properly focusing in at least two different portions of the eye.

12 Claims, 3 Drawing Sheets

OPHTHALMOLOGICAL INSTRUMENT

This application is a continuation of application Ser. No. 07/513,275 filed Apr. 24, 1990, now abandoned.

BACKGROUND OF THE INVENTION

1. Field of the Invention

This invention relates to an ophthalmological instrument having an anterior portion observation optical system for observing the anterior portion of an eye to be tested.

2. Discussion of the Related Art

A conventional ophthalmological instrument, for example, a noncontact type tonometer, having an anterior portion observation system for observing the anterior portion of an eye to be tested is known. This anterior portion observation system is adapted to make it easy to perform the positional adjustment or the so-called alignment verification of the instrument with respect to the eye to be tested.

In this type of the instrument, an optical system for observing the anterior portion of the eye to be tested is provided so that an image of the anterior portion of the eye to be tested is formed on a predetermined imaging plane when the distance between the eye to be tested and the instrument is proper. Owing to the foregoing, in order to perform the alignment verification, the instrument may be in a position close enough to the eye to be tested so that the image of the anterior portion of the eye to be tested can be observed approximately. For this purpose, after the instrument is gradually brought closer to the eye into eye to be tested first in order to bring into the focus, an optical axis is aligned and the distance is correctly adjusted.

In this conventional instrument, for example, in a non-contact type tonometer, a proper working distance between a nozzle for ejecting air and the cornea of the eye to be tested is approximately 11 mm. The anterior portion of the eye is not seen until the instrument approaches this distance and therefore, the adjustment is performed by feel until the instrument is brought close to the eye so that the anterior portion can be seen to some extent. This adjustment requires much time and professional skill.

SUMMARY OF THE INVENTION

An object of the present invention is to provide an ophthalmological instrument such that those who are not skilled persons can perform correct alignment verification in a short time.

Another object of the invention is to provide an ophthalmological instrument in which the anterior portion of the eye to be tested can be observed in a properly focused state even if the eye testing unit is moved.

A further object of the invention is to provide an ophthalmological instrument in which the anterior portion of the eye to be tested can always be observed in a properly focused state by moving a focus lens in accordance with movement of an eye testing unit.

A feature of the present invention is that an anterior portion observation system is provided with focusing position shifting means capable of focusing in at least two different positions of the eye to be tested.

Another feature of the present invention is that: an anterior portion observation system is provided with focusing position shifting means capable of focusing in at least two different positions of the eye testing unit with reference to the anterior portion of the eye to be tested.

A further feature of the present invention is that the anterior portion observation system is provided with a focusing lens which is moved in accordance with movement of the eye testing unit and properly focused on the anterior portion of the eye to be tested.

DETAILED DESCRIPTION OF THE PREFERRED EMBODIMENTS

The embodiment of the present invention will be described with reference to the drawings.

Figure 1:
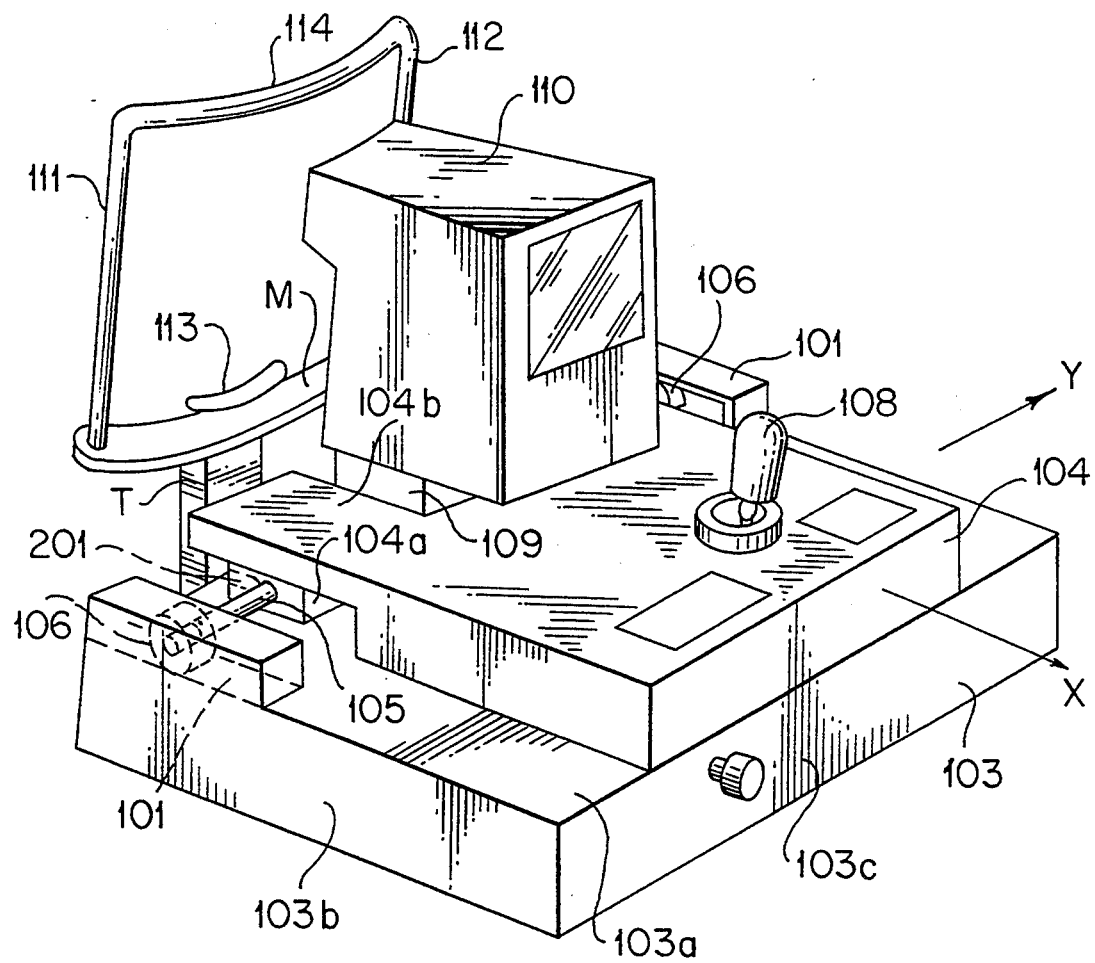
FIG. 1(A) is a perspective view of an ophthalmological instrument according to the present invention.
FIG. 1(B) is a sectional view showing a guide rail.
Figure 1:
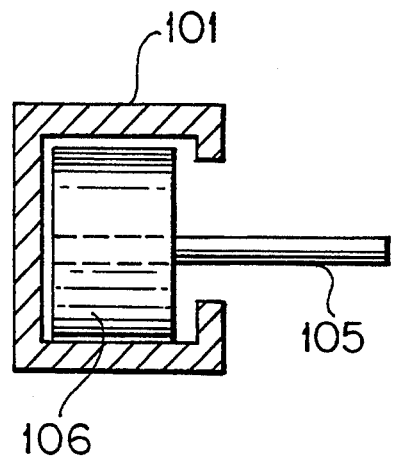

In FIG. 1(A), a mounting base 103 is provided with a pair of guide rails 101 mounted on both ends thereof and extending in the forward and backward direction, Each of the guide rails 101, as shown in FIG. 1(B), is formed in a C-shape in section. A mounting platform 104 is mounted on the mounting base 103, and a front end side 104b of the mounting platform 104 is disposed between the pair of guide rails 101.

On a lower surface of the front, end side 104b of the mounting platform 104, a bearing 104a is secured. A shaft 105 rotatably penetrates the bearing 104a. The bearing 104a can be slid along the shaft 105. That is, the mounting platform 104 can be slid in the lateral direction (Y-axis direction) along the shaft 105.

Each end portion of the shaft 105 is inserted into the guide rails 101 as shown in FIG. 1(B). A wheel 106 is fixedly secured to each end portion of the shaft 105 so that the wheel 106 can be rolled and moved within the guide rail 101. Because of the rolling movement of the wheel 106, the mounting platform 104 can be moved in the forward and backward direction (X-axis direction).

A rear portion of the mounting platform 104 is provided with a joy stick 108 adapted to finely move the mounting platform 104 in the forward and backward, right and left directions. A noncontact type tonometer as an eye testing unit 110 is mounted on an upper part of the mounting platform 104 through a supporting column 109.

In accordance with the movement of the mounting platform 104 in the directions of X- and Y-axes, the eye testing unit 110 is moved in the directions of X- and Y axes together with the mounting platform 104.

A supporting column T is mounted on a front end portion of the mounting base 103, and a supporting plate M extending in the horizontal direction is mounted on an upper end of the supporting column T. A pair of supporting posts 111 and 112 are fixedly erected on both ends of the supporting plate M. The supporting member M between the supporting posts 111 and 112 is provided with a jaw resting member 113, and a head portion abutting bar 114 is stretched between the supporting posts 111 and 112 at upper end portions thereof.

The bearing 104a is provided with a pulse generator 201 for generating a pulse every time the guide shaft 105 rotates a predetermined angle. The pulse generator 201 is adapted to detect a position of the mounting platform 104 in the direction of the X-axis.

Figure 2:
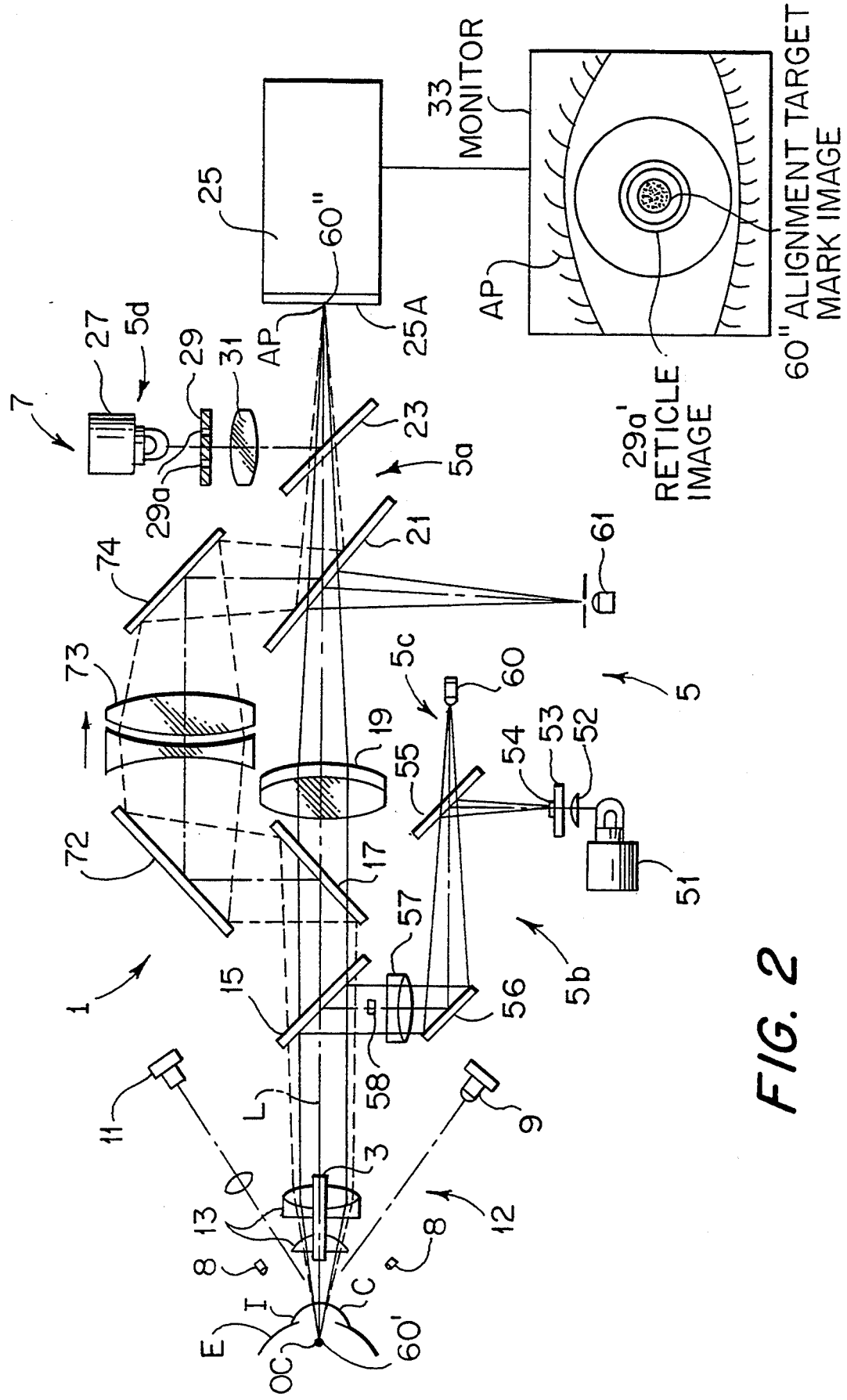
FIG. 2 is a view showing the arrangement of an optical system of the ophthalmological instrument.

FIG. 2 is a view showing an arrangement of the optical systems of the noncontact type tonometer 1.

This noncontact type tonometer 1 includes, if roughly classified, an intraocular pressure measurement system 12 having an air pulse ejecting nozzle 3 for ejecting an air pulse (air jet stream) toward the cornea c of the eye E, an alignment verification system 5 for verifying alignment of the instrument with respect to the eye E, and an anterior portion observation system 7 for optically observing the anterior portion of the eye E.

The intraocular pressure measurement system 12 includes a light projector 9 for projecting light to the cornea at the time when the intraocular pressure is measured, and a light receiving device 11 for receiving light from the light projector 9 reflected by the cornea c.

The alignment verification system 5 includes an alignment light image receiving optical system 5a, a sight fixation mark projection system 5b, an alignment light projection optical system 5c, and a reticle projection system 5d.

The alignment light image receiving optical system 5a has its optical axis coaxially arranged with an axial line L of the air pulse ejecting nozzle 3, and objective lens 13, a half mirror 15, a dichroic mirror 17, a telephoto lens 19, and two dichroic mirrors 21 and 23 are arranged in this order from the eye E.

The dichroic mirrors 17 and 23 are adapted to reflect visible light and permit infrared light to transmit therethrough. The dichroic mirror 21 is designed to reflect visible light and act as a half mirror with respect to infrared light.

Also, in the sight fixation mark projecting system 5b, a part of its optical axis is coaxially arranged with an optical axis of the alignment light image receiving optical system 5a, and light from a visible light source 51 is condensed by a condenser lens 52 and illuminates a sight fixation mark 54 formed on a sight fixation mark plate 53.

Light from the sight fixation mark plate 53 is reflected by a dichroic mirror 55 of the type for reflecting visible light and permitting infrared light to transmit therethrough, then reflected by the mirror 56, the collimator lens 57, and the half mirror 15 to form parallel rays of light, and then directed to penetrate the air pulse ejection nozzle 3 so as to be projected to the eye E.

In case the eye E suffers from myopia or hyperopia, a diopter correction lens 58 is inserted into the optical path of the sight fixation mark projection system 5b.

Furthermore, almost all of the component elements of the alignment light projection optical system 5c are commonly used with the component elements of the sight fixation mark projection system 5b.

That is, light emitted from an infrared light emitting diode 60 as an alignment target mark is transmitted through the dichroic mirror 55, and then projected to the cornea c through the mirror 56, the collimator lens 57, the half mirror 15, and the objective lens 13.

At this time, it is set such that a virtual image 60' of an alignment target mark is formed in the center OC of curvature of the cornea c by the objective lens 13.

Target light reflected by the cornea c is reverses direction on the projection optical path of the alignment target mark 60 as if the target light were emitted from the virtual image 60', then is made into a parallel beam of light by the objective lena 13, then is permitted to transmit through the half mirror 15, the dichroic mirror 17, the telephoto lens 19, and the two dichroic mirrors 21 and 23, and then arrives at a photosensitive surface 25A of a TV camera 25.

Accordingly, an image 60" of the alignment target mark is formed on the photosensitive surface 24A by the telephoto lens 19, and the image 60" is displayed on a monitor 33.

At the same time, the alignment target light is reflected on a infrared half mirror surface of the dichroic mirror 21, made incident to a detector 61 for detecting infrared light, which then detects an alignment completion state. Then, a working trigger signal is sent to a known air puff ejection system from the detector 61.

Next, in the reticle projection system 5d, a part of the optical axis is aligned with the optical axis of the alignment light image receiving optical system 5a, and light from a visible light source 27 is caused to illuminate a reticle plate 29 having a reticle target mark 29a.

Light transmitted through the reticle target mark 29a is reflected by an imaging lens 31 at the dichroic mirror 23, and then imaged on the photosensitive surface 25A of the TV camera 25, and the image is displayed on the monitor 33 as the reticle image 29a.

The alignment operation is performed by moving the entire instrument upward and downward, right and left, to that the position of the alignment target mark image 60" is brought to the center of the reticle image 29a' of the monitor 33. Also, the working distance (distance between the air pulse ejection nozzle 3 and the cornea c) is adjusted by moving the entire instrument forward and backward so that the alignment target mark image 60" becomes a sharp image.

Next, in the anterior portion observation system 7, a part of the optical axis is coaxial with the axial Line L of the air pulse ejection nozzle 3. Accordingly, a part of the optical axis of the anterior portion observation system 7 is coaxial with a part of the optical axis of the alignment optical system 5.

The anterior portion observation system 7 comprises a pair of visible light emitting light sources, 8 disposed on both sides of the axial line L and adapted to illuminate the anterior portion, the objective lens 13, the dichroic mirror 17, a mirror 72, a reduction projection system lens group 73, a mirror 74, and the dichroic mirror 21.

This reduction projection system lens group 73 is designed such that the anterior portion of the eye E, particularly an image of the iris I, is formed on the photosensitive surface 25A of the TV camera 25 in its reduced scale.

Accordingly, a visible light reflected by the anterior portion illuminated by the light source 8 is condensed by the objective lens 13, then transmitted through the half mirror 15 and reflected by the dichroic mirror 17 and the dichroic mirror 72.

After being transmitted through the reduction projection system lens group 73, the reflected light is reflected by the dichroic mirror 21, and therefore, the reflected light, when transmitted through the dichroic mirror 23, is imaged on the photosensitive surface 25A by the reduction projection system lens group 73, and its image (anterior portion image) AP is displayed on the monitor 33.

By the way, the reduction projection system lens group 73 is movable in the direction as shown by an arrow in such a manner as to be interlocked with the movement of the mount platform 104 in the direction of the X-axis, so that the anterior portion can always be observed in a properly focused state. That is, even if the eye testing unit 110 is away from the proper working distance with respect to the eye E, the anterior portion of the eye E can be observed in a properly focused state.

Figure 3:
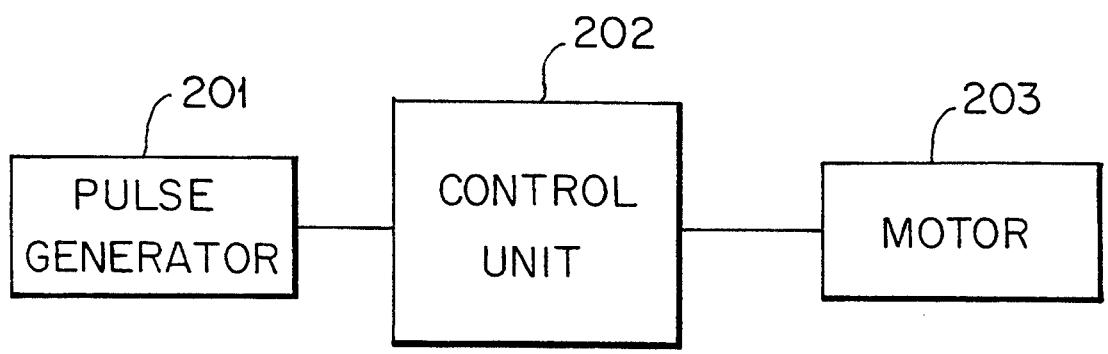
FIG. 3 is a block diagram showing the construction of a control system for moving a lens group of a reduction projection system.

The movement of the reduction projection system lens group 73 is performed by a motor 203, etc. as shown in FIG. 3. In this case, a pulse generated from a pulse generator 201 is counted by a control unit 202 to detect the position of the mounting platform 104, i.e., position of the eye testing unit 110, and the motor 203 is controlled by the control unit 202 so that the motor 203 causes the reduction projection system lens group 73 to move in such a manner as to properly focus in such detected position. The motor 203 and the reduction projection system lens group 73 form the focus position shifting means.

In this way, even when the eye testing unit 110 is in a position away from the eye E, the anterior portion of the eye E can be observed in a properly focused state. Accordingly, the optical axis can be roughly aligned at an early stage, and thereafter accurate alignment of the optical axis and an adjustment of the working distance can be performed efficiently. As a consequence, even those who are not skilled persons can perform an accurate alignment in a short time.

In the above embodiment, although it is designed such that the anterior portion can always be observed in a properly focused state by moving the reduction projection system lens group 73 following the movement of the mounting platform 104, the present invention is not limited to this.

For example, it may be designed such that the reduction projection system lens group 73 can be shifted to first and second positions, so that a properly focused skate can be obtained in both cases where the reduction projection system lens group 73 is brought to the first position when the mounting platform 104 is in a position where the alignment is completed, and where the reduction projection system lens group 73 is brought to the second position when the mounting platform 104 is one-sided toward the inspector. In this way, if the reduction projection system lens group 73 is shifted to the second position, the alignment, etc. of the optical axis can be performed while observing the anterior portion of the eye E in the manner am mentioned above. In this case, the shifting of reduction projection system lens group 73 may be performed by a microswitch which is activated by movement of the mounting platform 104.

Instead of moving the reduction projection system lens group 73, the present invention alternatively may be designed such that the lens is exchanged, an additional lens is inserted, or the TV camera 25 itself is moved in the direction of the optical axis.

What is claimed is:

1. An ophthalmological instrument comprising:
   a base means;
   an eye-testing unit disposed on the base means facing an eye to be tested, including an anterior portion observation system for observing an anterior portion of an eye,
   said anterior portion observation system having a focusing position shifting means for properly focusing on the anterior portion of the eye in at least two different defined positions of said eye-testing unit;
   shift mechanism means for shifting said eye-testing unit on said base in a forward and backward direction with respect to the eye to be tested to establish one of the at least two different defined positions; and
   means responsive to the shift mechanism means for operating the focusing position shifting means as a function of movement of the eye testing unit.

2. The ophthalmological instrument of claim 1, wherein said focus position shifting means comprises a reduction projection system lens group.

3. An ophthalmological instrument comprising:
   a base;
   an eye-testing unit disposed on the base facing an eye to be tested, said eye-testing unit including an anterior portion observation system for observing an anterior portion of the eye;
   said anterior portion observation system including a focusing lens and focusing lens movement means;
   shift mechanism means for shifting said eye-testing unit on said base forwards and backwards with respect to the eye to be tested to establish a desired position of said eye-testing unit; and
   means responsive to the shift mechanism means for operating the focusing lens movement means as a function of the eye-testing unit to properly focus on the anterior portion of the eye to be tested.

4. An ophthalmological instrument comprising:
   a base;
   an eye-testing unit disposed on the base facing an eye to be tested including an observation system for observing the anterior portion of the eye to be tested, said anterior portion observation system including
   a focusing lens for properly focusing on the anterior portion of the eye to be tested,
   a pulse-generating means for generating a pulse each time said eye-testing unit moves by a predetermined amount,
   a counting means for counting said pulses, and
   a focusing lens driving means for driving said focusing lens according to the number of pulses counted by the counting means; and
   a shift mechanism which shifts said eye-testing unit on said base forwards and backwards with respect to the eye to be tested.

5. The ophthalmological instrument of claim 4, wherein said shift mechanism comprises a pair of guide rails and a corresponding pair of wheels.

6. The ophthalmological instrument of claim 4, wherein said focus lens driving means comprises a motor.

7. An ophthalmological instrument comprising:
   a base means;
   an eye-testing unit disposed on the base means facing an eye to be tested including an anterior portion observation system for observing the anterior portion of the eye, said anterior portion observation system being provided with a focusing position shifting means for properly focusing on the anterior portion of the eye in at least two different positions that can be changed by said eye-testing unit, said focusing position shifting means comprising a reduction projection system lens group and a motor for moving the reduction projection system lens group; and
   shift mechanism means for shifting said eye-testing unit on said base in a forward and backward direction with respect to the eye to be tested.

8. An ophthalmological instrument comprising:
   a base means;

an eye-testing unit disposed on the base means facing an eye to be tested including an anterior portion observation system for observing the anterior portion of the eye, said anterior portion observation system being provided with a focusing position shifting means for properly focusing on the anterior portion of the eye in at least two different positions that can be changed by said eye-testing unit; and shift mechanism means for shifting said eye-testing unit on said base in a forward and backward direction with respect to the eye to be tested comprising a pair of guide rails and a corresponding pair of wheels.

9. An ophthalmological instrument comprising:
a base;
an eye-testing unit disposed on the base facing an eye to be tested, said eye-testing unit including an anterior portion observation system for observing the anterior portion of the eye, said anterior portion observation system including a focusing lens and a focusing lens movement means for moving the focusing lens corresponding to the movement of the eye-testing unit to properly focus on the anterior portion of the eye to be tested, said focusing lens movement means comprising a control unit and a motor; and shift mechanism means for shifting said eye-testing unit on said base forwards and backwards with respect to the eye to be tested.

10. An ophthalmological instrument comprising:
a base;
an eye-testing unit disposed on the base facing an eye to be tested, said eye-testing unit including an anterior portion observation system for observing the anterior portion of the eye, said anterior portion observation system including a focusing lens and a focusing lens movement means for moving the focusing lens corresponding to the movement of the eye-testing unit to properly focus on the anterior portion of the eye to be tested; and shift mechanism means for shifting said eye-testing unit on said base forwards and backwards with respect to the eye to be tested, said shift mechanism comprising a pair of guide rails and a corresponding pair of wheels.

11. An ophthalmological instrument comprising:
a base;
an eye-testing unit disposed on the base facing an eye to be tested including an anterior portion observation system for observing the anterior portion of the eye, said anterior portion observation system including
a focusing lens which is movable according to the movement of the eye-testing unit to properly focus on thee anterior portion of the eye to be tested,
a position detecting means which detects the position of said eye-testing unit, and
a focusing lens driving means for driving said focusing lens according to the position of the eye-testing unit detected by the position detecting means to properly focus on the anterior portion of the eye, said focusing lens driving means comprising a control unit and a motor; and shift mechanism means for shifting said eye-testing unit on said base forwards and backwards with respect to the eye to be tested.

12. An ophthalmological instrument comprising:
a base;
an eye-testing unit disposed on the base facing an eye to be tested including an anterior portion observation system for observing the anterior portion of the eye, said anterior portion observation system including
a focusing lens which is movable according to the movement of the eye-testing unit to properly focus on the anterior portion of the eye to be tested,
a position detecting means which detects the position of said eye-testing unit, and
a focusing lens driving means for driving said focusing lens according to the position of the eye-testing unit detected by the position detecting means to properly focus on the anterior portion of the eye; and shift mechanism means for shifting said eye-testing unit on said base forwards and backwards with respect to the eye to be tested, said shift mechanism comprising a pair of guide rails and a corresponding pair of wheels.

* * * * *